(12) United States Patent
Zhu et al.

(10) Patent No.: US 10,166,004 B2
(45) Date of Patent: Jan. 1, 2019

(54) ULTRASOUND CONTRAST IMAGING METHOD AND APPARATUS

(71) Applicant: SHENZHEN MINDRAY BIO-MEDICAL ELECTRONICS CO., LTD., Shenzhen (CN)

(72) Inventors: Ziyan Zhu, Shenzhen (CN); Maodong Sang, Shenzhen (CN); Yongqiang Dong, Shenzhen (CN)

(73) Assignee: SHENZHEN MINDRAY BIO-MEDICAL ELECTRONICS CO., LTD., Shenzhen (CN)

( * ) Notice: Subject to any disclaimer, the term of this patent is extended or adjusted under 35 U.S.C. 154(b) by 223 days.

(21) Appl. No.: 14/749,292

(22) Filed: Jun. 24, 2015

(65) Prior Publication Data

US 2017/0071574 A1   Mar. 16, 2017

Related U.S. Application Data

(63) Continuation of application No. PCT/CN2013/083890, filed on Sep. 22, 2013.

(30) Foreign Application Priority Data

Dec. 24, 2012 (CN) .......................... 2012 1 0566296

(51) Int. Cl.
    *A61B 8/08*     (2006.01)
    *G01S 7/52*     (2006.01)
    (Continued)

(52) U.S. Cl.
    CPC ............ *A61B 8/481* (2013.01); *A61B 8/0891* (2013.01); *A61B 8/461* (2013.01); *A61B 8/5207* (2013.01);
    (Continued)

(58) Field of Classification Search
    CPC ...................................................... A61B 8/481
    See application file for complete search history.

(56) References Cited

U.S. PATENT DOCUMENTS

| 2006/0067567 A1* | 3/2006 | Hashimoto | A61B 8/13 |
| | | | 382/131 |
| 2009/0099452 A1 | 4/2009 | Hashimoto | |
| 2009/0204003 A1* | 8/2009 | Guracar | A61B 8/06 |
| | | | 600/458 |

FOREIGN PATENT DOCUMENTS

| CN | 1658798 A | 8/2005 |
| CN | 1754511 A | 4/2006 |

* cited by examiner

*Primary Examiner* — Nate Sunwoo
(74) *Attorney, Agent, or Firm* — Polsinelli LLP; Kory D. Christensen (57) ABSTRACT

An ultrasonic contrast imaging method and apparatus thereof. The method includes acquiring N frames of contrast image in an imaging period; projecting the N frames of contrast image to obtain a projection result image of the N frames of contrast image, wherein an nth group of original contrast image is projected in a projection template to obtain a projection result image of an nth frame of original contrast image, wherein the projection template is one frame of the nth group of original contrast image, and n is a positive integer greater than or equal to 1 and less than or equal to N, wherein the nth group of original contrast images is within a projection period and includes the nth original contrast image, and the projection period is a fixed value less than the imaging period; and displaying or storing the projection result image.

15 Claims, 11 Drawing Sheets

(51) Int. Cl.
  *G01S 15/89* (2006.01)
  *A61B 8/00* (2006.01)
  *A61B 8/13* (2006.01)
(52) U.S. Cl.
  CPC .......... *A61B 8/5269* (2013.01); *A61B 8/5276* (2013.01); *G01S 7/52034* (2013.01); *G01S 7/52039* (2013.01); *G01S 15/8993* (2013.01); *A61B 8/13* (2013.01)

ULTRASOUND CONTRAST IMAGING METHOD AND APPARATUS

TECHNICAL FIELD

The present disclosure relates to ultrasonic imaging, in particular to ultrasonic contrast imaging method and apparatus thereof.

BACKGROUND

Medical ultrasonic imaging usually utilizes reflection of ultrasound at the interface of body tissues, receives and processes the echo containing characteristic information of the boy tissue to obtain a visible ultrasound image thereof. However, it may difficult to view small blood vessels in color Doppler imaging due to reverberation, restriction of the resolution, low vascular flow or low velocity of the vascular flow in the small blood vessels, sometimes the mall blood vessels are blurring or even cannot be found in the ultrasound image. Ultrasonic contrast imaging is now utilizes to make the blood flow imaging sharper by using contrast agent to enhance the back-scattering, which can help practitioners identifying and diagnosing particular diseases. Generally, contrast imaging micro-bubbles in the small blood vessel can reflect the structure thereof. However, if the diameter of the small blood vessel is close to the contrast imaging micro-bubbles, there will be few micro-bubbles in the small vessel, and that can result in unstable contrast imaging and the micro-bubbles are likely identified as random speckles in the image.

Conventional ultrasonic imaging includes the steps of converting electrical signals into ultrasound through a probe, transmitting the ultrasound to the target object, receiving the reflected and scattered echo beams from the target object, the echo beams then can be converted to electrical signals. A DSC (Digital Scan Conversion) and image post processing step can be performed after the electrical signal being signal processed, and the images obtained by the processing steps can be displayed or stored at last. In an ultrasonic imaging system utilizing contrast agents, an imaging processing unit is usually introduced before or after the DSC. For example, the imaging processing unit can utilize a MIP (Maximum Intensity Projection) method to reflect micro vascular morphology by accumulating flow paths of the contrast micro-bubbles in the small blood vessel. The principle of the MIP imaging can be described as: acquiring a plurality of frames of contrast image, and a pixel with maximum brightness (intensity) among the spatial corresponding pixels in each frame of image can be projected to a fixed template image. After the MIP processing, the contrast images of the micro-bubbles in multi-frame contrast image can be connected in the fixed template image, and the detected structure of the small blood vessels is finally outputted.

MIP operations may described according to the following equation (1):

$$\text{outputPixel}(x,y,n) = \max(\text{inputPixel}(x,y,1), \text{inputPixel}(x,y,2), \ldots, \text{inputPixel}(x,y,n)) = \max(\text{inputPixel}(x,y,n), \text{outputPixel}(x,y,n-1)) \quad (1)$$

wherein, inputPixel (x, y, 1) represents the actual luminance of a pixel with coordinates (x, y) of the first frame input image, inputPixel (x, y, 2) represents the actual luminance of a pixel with coordinates (x, y) of the second frame input image, . . . , and so on, thus inputPixel (x, y, n) represents the actual luminance of a pixel with coordinates (x, y) of the nth frame input image, and 1,2, . . . N represents time sequence; similarly, outputPixel (x, y, n−1) represents the displayed luminance of a pixel with coordinates (x, y) of the n−1th frame output image, and outputPixel (x, y, n) represents the displayed luminance of a pixel with coordinates (x, y) of the nth frame output image.

Figure 1:
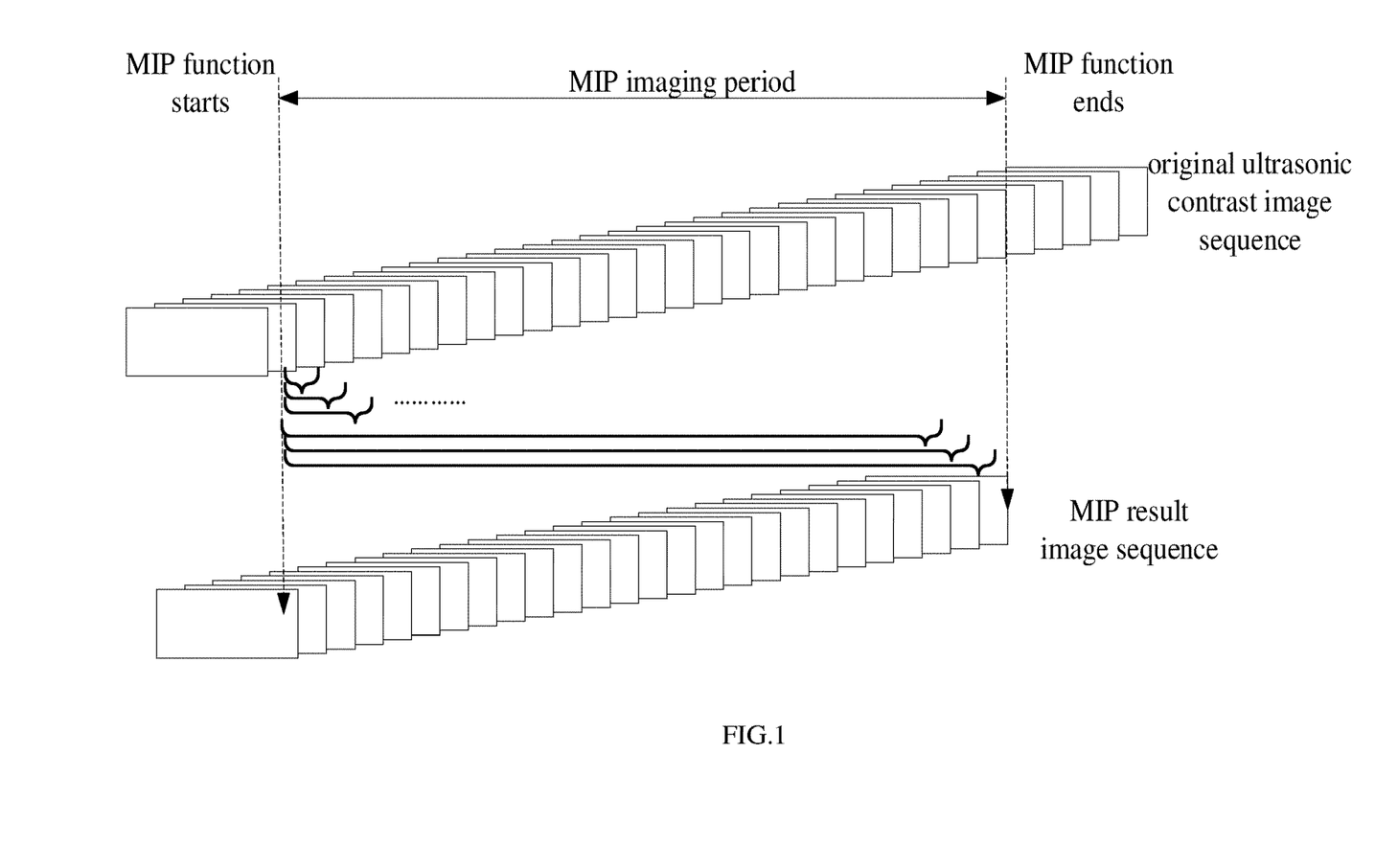
FIG. 1 is a schematic diagram of conventional MIP imaging technique.

The popular commercial ultrasonic imaging equipment usually have the function of continuous contrast imaging, although the names are different but the imaging principles are all based on the MIP imaging method. Those conventional MIP methods are referred to as conventional MIP in this disclosure. Please refer to FIG. 1, the upper row of rectangular frames represent an original ultrasonic contrast image sequence, the lower row of rectangular frames represent a MIP result image sequence using the conventional MIP. The input image at the MIP processing start point (shown as the "MIP function starts") can be selected as the fixed MIP projection template, and the MIP projection period is shown as inverted brackets, each of the brackets denotes a projection period. Accordingly, the projection periods increase gradually in the conventional MIP, from the starting point of the MIP process to the ending point (shown as the "MIP function ends"), and finally, MIP projection period is equal to the MIP imaging period. MIP process starting point and ending point are usually system default or user-selected. That is, the maximum luminance value of all selected image sequence is projected onto the first frame image (the template image).

Conventional MIP imaging techniques are capable of providing spatial information of existence lesions or regions of interest, such as morphology of the small blood vessels, but meanwhile part of the time information are lost, such as fade time of contrast agents. The time information of the suspected lesion, such as fast-forward and fast-rewind, or fast-forward but slow rewind, can help doctors diagnosing whether the tumor is benign or malignant. On the other hand, the conventional MIP imaging technology is a contrast image accumulation and overlay technology, the longer the projection period, the larger the cumulative error, such that the contrast of the vessels and tissue decline, and the MIP imaging result becomes worse.

SUMMARY

This disclosure provides an ultrasonic imaging apparatus and method for ultrasonic imaging a target object injected with contrast agent bubble.

According to a first aspect of the disclosure, the disclosure provides an ultrasonic contrast imaging method includes an initial step for acquiring N frames of contrast image, and N is the total number of frames of an imaging period; a projection imaging step for projecting the N frames of contrast image to obtain projection result image of the N frames of contrast image, wherein an nth group of original contrast image is projected in a projection template to obtain a projection result image of an nth frame of original contrast image, wherein the projection template is one frame of the nth group of original contrast image, and n is a positive integer greater than or equal to 1 and less than or equal to N, wherein the nth group of original contrast images is within the projection period and comprises a plurality of frames of original contrast images which comprising the nth original contrast image, the projection period is a fixed value less than the imaging period; and a display and/or storage step for displaying or storing the projection result image of the N frames of original contrast image.

According to a second aspect of the disclosure, the disclosure provides an ultrasonic contrast imaging apparatus includes: an original image acquisition unit for emitting ultrasonic pulse to a target object, receiving ultrasonic echo signals returned by the target object, performing signal processing to the received ultrasonic echo signals to obtain N frames of contrast image, and N is the total number of frames of an imaging period; a projection imaging unit for projecting the N frames of contrast image to obtain projection result image of the N frames of contrast image, wherein an nth group of original contrast image is projected in a projection template to obtain a projection result image of an nth frame of original contrast image, wherein the projection template is one frame of the nth group of original contrast image, and n is a positive integer greater than or equal to 1 and less than or equal to N, wherein the nth group of original contrast images is within the projection period and comprises a plurality of frames of original contrast images which comprising the nth original contrast image, the projection period is a fixed value less than the imaging period; and a display/storage unit for displaying or storing the projection result image of the N frames of original contrast image.

DETAILED DESCRIPTION

The present application will be further described by the following detailed description of specific embodiments with the accompanying drawings.

For ease of understanding, some terms used in this disclosure are firstly introduced as following.

(1) Imaging Period: refers to the duration from the start of the image persistence processing function to the end of the function, such as duration from start executing of the projection imaging unit of the ultrasonic contrast imaging apparatus of the present disclosure to end executing it. The unit can be set, but is not limited to time (for example, one second, two seconds, three seconds . . .) or image frames (such as ten frames, twenty frames, thirty frames . . .). (2) Projection Period: In the imaging period, each frame of developed image is a output result by continuously processing a plurality frames of original contrast image sequence over a period of time or of certain number of frames, the period of time or frame can be defined as the "projection period", and similarly, the unit can be set, but is not limited to time (for example, one second, two seconds, three seconds . . .) or image frames (such as ten frames, twenty frames, thirty frames . . .). In the present disclosure, the projection period is less than the imaging period.

Figure 2:
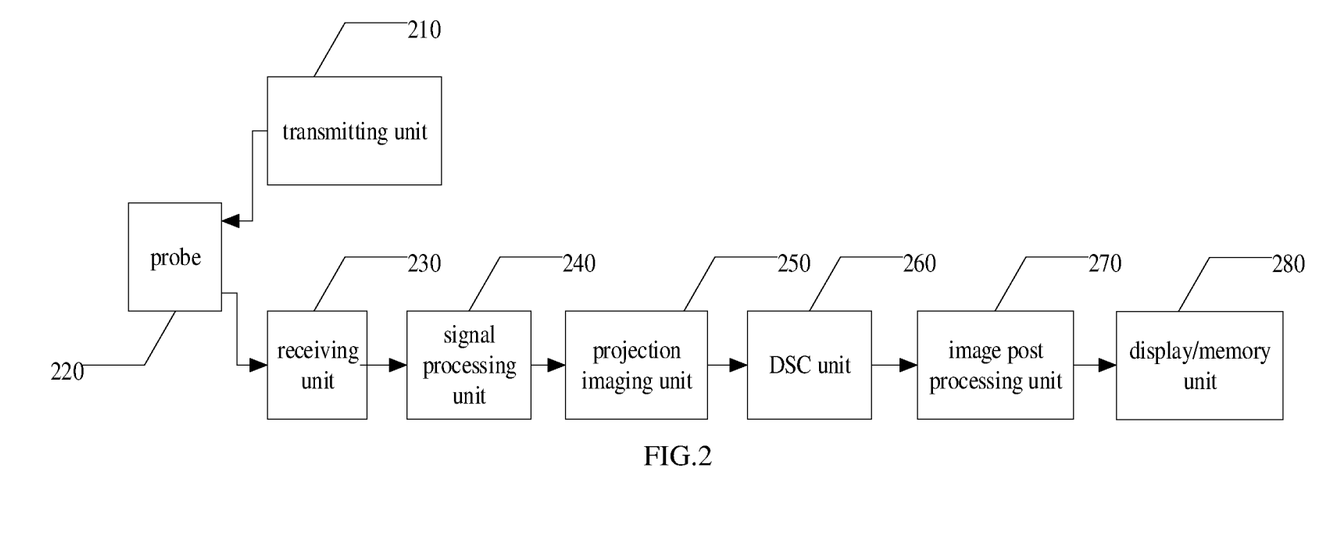
FIG. 2 is a structural diagram of an ultrasonic contrast imaging apparatus according to one embodiment of the present disclosure.

FIG. 2 is a structural diagram of an ultrasonic contrast imaging apparatus according to one embodiment of the present disclosure. A transmitting unit 210 transmits ultrasonic waves through a probe 220. The ultrasonic waves enter the body, then reflected by contrast agents and tissues of the human body, and received by a receiving unit 230. The received echo signals can be processed by a signal processing unit 240, and transmitted to a projection imaging unit 250 for further processing. The processed image data can be processed by a DSC unit 260 and a image post processing unit 270, and finally be transmitted to a display/storage unit 280 for display or storage. The transmitting unit 210, the probe 220, the receiving unit 230, the signal processing unit 240, the DSC unit 260, the image post processing unit 270 and the display/storage unit 280, are available by corresponding function units of a conventional ultrasonic imaging system. For example, the receiver unit 230 may include an amplifier circuit, an A/D converter, etc. The signal processing unit 240 may include a Doppler processing function. The image post processing unit 270 may have a background suppression or spot elimination function. It will not be described in detail herein. In this embodiment, the projection imaging unit 250 is positioned before the DSC unit 260, but in other embodiments, the projection imaging unit 250 may also be positioned after the DSC unit 260 and before the display unit 280.

Based on the described embodiment of ultrasonic contrast imaging apparatus, the present disclosure also provides an ultrasonic contrast imaging method. The ultrasonic contrast imaging method will be described in detail by the following embodiments, and the imaging projection unit can also be reflected according to corresponding embodiment of the method.

Figure 3:
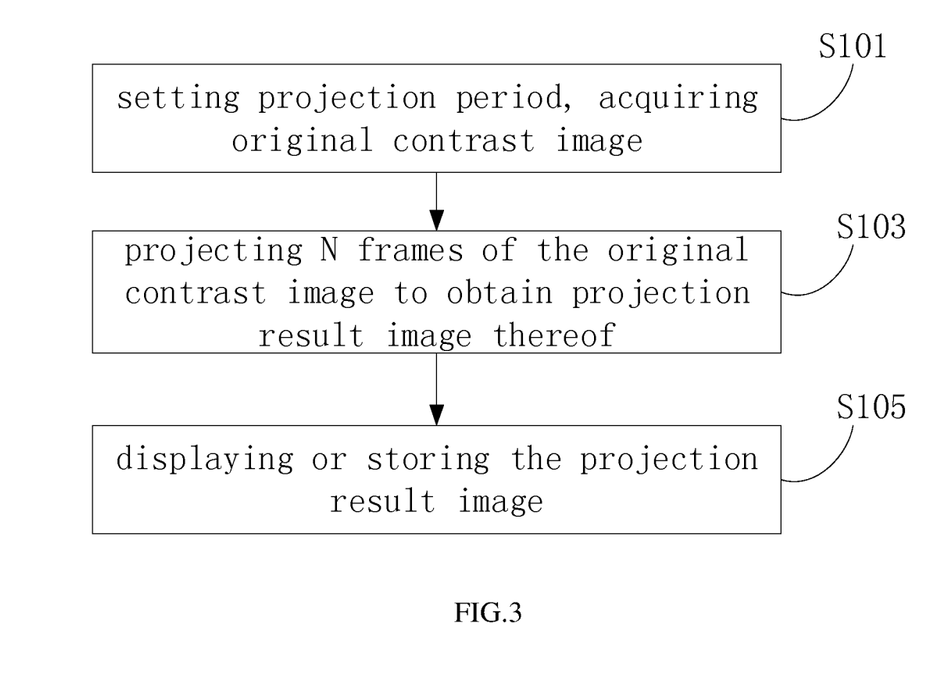
FIG. 3 is a schematic flow diagram of an ultrasonic contrast imaging method according to one embodiment of the present disclosure.

Embodiment 1:

As shown in FIG. 3, the ultrasonic contrast imaging method of the present embodiment includes steps S101-S105:

An initial step S101, setting the projection period, obtaining N frames of original contrast image, and N is the total number of frames of the imaging period. Details of obtaining the original contrast image can refer to conventional ultrasonic imaging methods, such as firstly emit ultrasonic pulses through the probe to the target object, the probe response to and receives the ultrasonic echo signals returned by the target object, then the system performs signal processing to the received echo signals to output original images over a plurality of time points. The original image may be the B-mode image (tissue image) or contrast image. In this disclosure, the specific structure of the probe and the process of transmitting and receiving, as well as the signal processing realized by corresponding function units of a conventional ultrasonic imaging system, which will not elaborate herein.

Projection imaging step S103, projects the N frames of the acquired original contrast image to obtain projection result images thereof. For one frame of the N frames of original contrast image, such as the nth frame of original contrast image, wherein n is a positive integer, and 1≤n≤N, a nth group of original contrast images can be projected to a projection template and the projection template can be any frame of the group, thus to obtain the projection results image of the nth frame of original contrast image. The nth group of original contrast images includes a plurality of frames of original contrast image in the projection period including the nth frame of original contrast image. Projection period of different groups of original contrast image may be identical, for example, all are ten or any other suitable number of frames. In other embodiments, the projection period of different groups of original contrast image also can be different, for example, the projection period of ith group of original contrast image is eight, but the projection period of jth group of original contrast image is ten, and i≠j, i and j are positive integers, 1≤i≤N, 1≤j≤N. Of course, the projection periods of ith group and jth group may be any other suitable value.

Projection operation can be expressed as equation (2):

$$\text{outputPixel}(x, y, n, k) = f(\text{inputPixel}(x, y, n), \text{inputPixel}(x, y, n-1), \ldots, \text{inputPixel}(x, y, n-k+1)) \quad (2)$$

In equation (2), outputPixel( ) represents the projection result image, inputPixel( ) represents the input original contrast image. Specifically, outputPixel(x, y, n, k) represents the gray value or luminance of the pixel with coordinate (x, y) in the nth frame of the projection result image, k represents the total number of frames of the projection period, f( ) denotes a specific function the projection imaging processing using, inputPixel (x, y, n) represents the gray value of the pixel with coordinate (x, y) in the nth frame of the input contrast image, inputPixel (x, y, n−1) represents the gray value of the pixel with coordinate (x, y) in the (n−1)th frame of the input contrast image, inputPixel (x, y, n−k+1) represents the gray value of the pixel with coordinate (x, y) in the (n−k+1th) frame of the input contrast image.

The function f( ) may include, but is not limited to the following:
(1) Time domain weighted integral calculation relate to image information, as the following equation (3):

$$\text{outputPixel}(x, y, n, k) = \sum Pi * \text{inputPixel}(x, y, n-i+1) \quad (3)$$

In equation (3), inputPixel (x, y, n) represents the information of the pixel with coordinates (x, y) in the input image, i.e., the current frame, or a projection template, outputPixel (x, y, n, k) represents the information of that pixel with coordinates (x, y) in the output image, i.e., the projection result image. Pi is a normalized weighting coefficient, that is, $\sum Pi = 1 = 1$. The weighting coefficient of each frame in the projection period can be identical, i.e., Pi=1/k, i=0~k−1, or with different weighting e.g., weighting of the current frame Pi is (2) Maximum, minimum, mean or median projection operations relate to image information. Take the maximum value projection operation as an example, and it can be described as the following equation (4):

$$\text{outputPixel}(x, y, n, k) = \max(\text{inputPixel}(x', y', n), \text{inputPixel}(x', y', n-1), \ldots, \text{inputPixel}(x', y', n-k+1)) \quad (4)$$

Parameters of equation (4) have the same meanings as the parameters of equation (2), and will not repeated herein.
(3) Functions relate to spatial frequency of the image.
(4) Functions relate to the total number of pixels of the contrast agent position in the image.
(5) Functions relate to 3D or 4D image.
(6) Other functions which need multi-frame image persistent synthesis process to reflect the space information and time information of the tissue.

In specific ultrasonic contrast imaging apparatus, this projection step can be started or shut down by a variety of ways, such as pre-set starting projection imaging processing when original image data is acquired, or the user can controls whether to perform the projection imaging through input devices such as keyboard, mouse or touch screen. Or ultrasonic device can adaptive start projection imaging processing according to the scanned organs or scan mode, such as start the projection imaging processing when performing the ultrasonic contrast imaging. Projection imaging steps may be performed in any case as follows:

(1) Performs the projection imaging step simultaneously when injecting the patient with contrast agents, the probe keep emitting ultrasonic beams with low sound pressure pulse;
(2) When the contrast micro bubbles have been filling into the scanning area, the probe emit high sound-pressure pulses to broke the contrast micro bubbles in part of the area; then restore low sound-pressure pulse emission beam to collect image information therefrom. In this case, if the high sound pressure pulse (MI) crushes the contrast micro bubbles in the imaging period of the projection imaging process, it may affect the projection imaging, and MI value of the probe emission can be automatically detected by the system, and automatically remove images with high MI values, or take the first frame of image when resumed to low MI value as the projection template, and restart projection imaging processing function.

Figure 4:
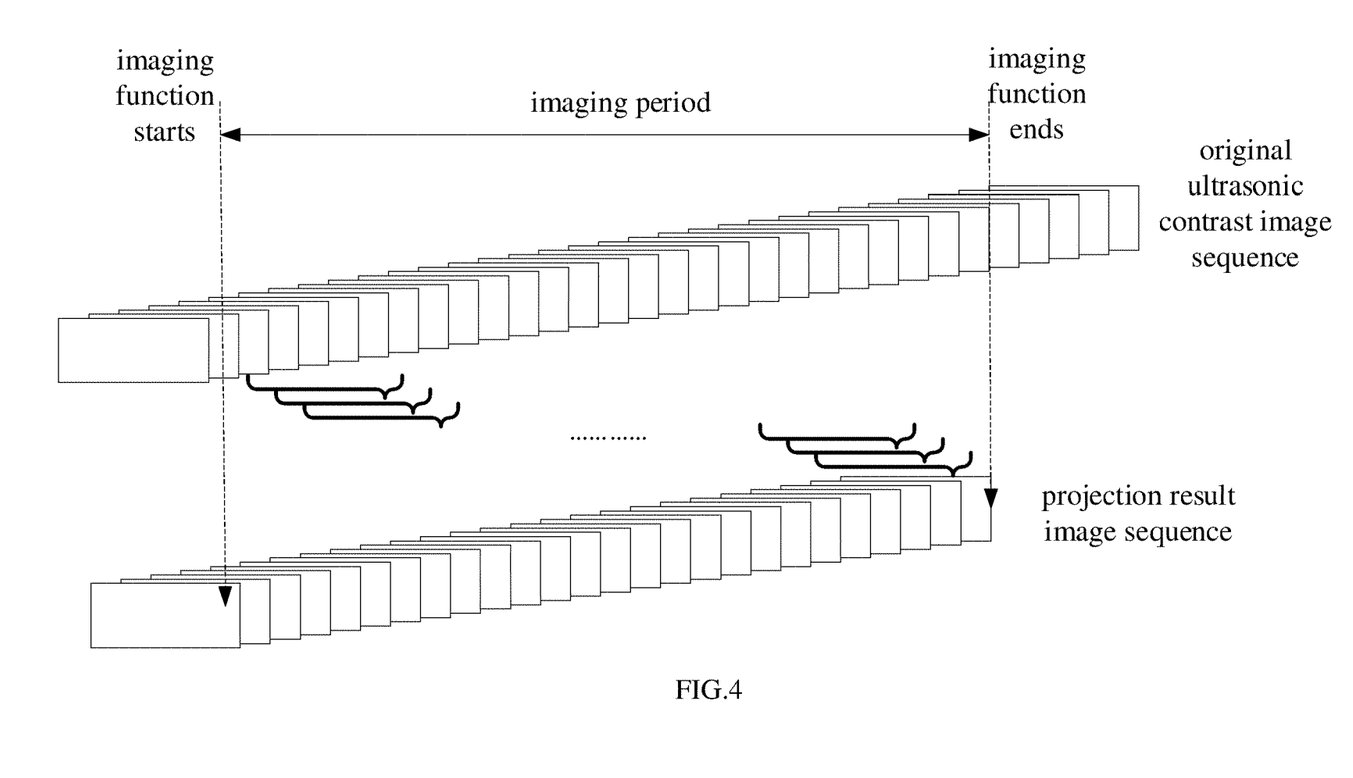
FIG. 4 is a principle diagram of a projection imaging method shown in FIG. 3.

The duration from the start of the projection imaging processing function to the end of the function is the imaging period, and the imaging period is equal to or greater than the projection period in this disclosure. As shown in FIG. 4, the upper row of rectangular frames represent an original ultrasonic contrast image sequence obtained in step S101, the lower row of rectangular frames represent a projection result image sequence according to the embodiments of this disclosure. The projection period is shown as inverted brackets, and each of the brackets denotes a projection period. These projection periods are fixed, and can be set as time or the number of frames, such as one second, two seconds, three seconds, etc., or by the number of frames such as 10 frames, 20 frames, 30 frames, etc.

In the ultrasonic imaging apparatus according to the embodiments, the value of the projection period can be obtained based on adaptive adjust by the apparatus according to scanned organ or scan mode, or can also be set in advance by the system, or can also be selected by user through option frame displayed on a user interface, and user can enter the selection through input device such as keyboard, mouse, or touch screen, or through physical element such as spin button. Changes of the projection period will affect imaging results. In an exemplary implementation, the ultrasonic device includes a control element for selecting projection period. The control element can provide a plurality of grade positions, such as a grade position of "OFF" means the projection imaging method utilizes the conventional MIP imaging method, that is, the projection period will be increased gradually until it equal to the imaging period. A grade position of "0" means the projection period is zero, and the projection result image is the projection template, that is, the projection result image equivalent to the contrast image. A grade position of "1s" means the projection result image is a persistent projection result of the projection template and frames during one second before the template's time. Similarly, a grade position of "2s" or "3s" also can be selected to vary the projection period. A grade position of "Auto" denotes the projection period is an adaptive value, and the corresponding projection result image is the persistent projection result adaptive adjusted by the system.

Effect of different projection imaging periods may be applied to different characteristics of blood vessel regression or filling, or to different pathological situations. For example, a shorter projection period, such as one second, may be applied to situation of blood quickly been filled or regressed quickly and rich of blood vessels. A longer projection period, such as three seconds may be applied to situation of blood quickly been filled or regressed slowly.

The way of selecting the projection template can be varied. It can be system default, or controlled by user through input device such as keyboard, mouse, or touch screen, or can be adjusted adaptively by the ultrasonic apparatus according to scanned organ or scan mode. Different projection template will have different image result. In the developing period, the projection template can be fixed or change over time. For the fixed projection template in the imaging period, the template can be the first frame of image after the imaging processing function started, as shown in FIG. 4. The image developing process reflects the static spatial information of the template frame image and the time information of the tissue structure over the whole imaging period. For example, take the first frame of image in the imaging period as a projection template, the static structure of the tissue during the first frame of image and the growth patterns of the contrast micro bubbles during the imaging period may be observed. Of course, you can also select any frame within the image developing period as a fixed projection template. For time-varying projection template within the imaging period, which refers to the projection template may be any one frame of the current projection period, that is, the imaging processing result can be projected onto any frame of image within the projection period. The image developing process can reflect the dynamic spatial information of the template frame image and limited time information of the tissue structure within the projection period. Assume the current frame is one frame of image within a projection period, and the current frame is set as the projection template, the dynamic spatial structure of the tissue in the scanning plane and growth patterns of the contrast micro bubbles in the tissue during the imaging period can be observed.

In order to better distinguish or compare, you can add color image information to the projection result image to reflect the developing time information of the contrast micro bubbles.

A projection result image sequence can be obtained by projection imaging processing entire original contrast images within the imaging period.

Displaying or storing step S105, the projection result images of the N frames of original contrast image obtained in imaging step S103 can be displayed or stored.

Figure 5:
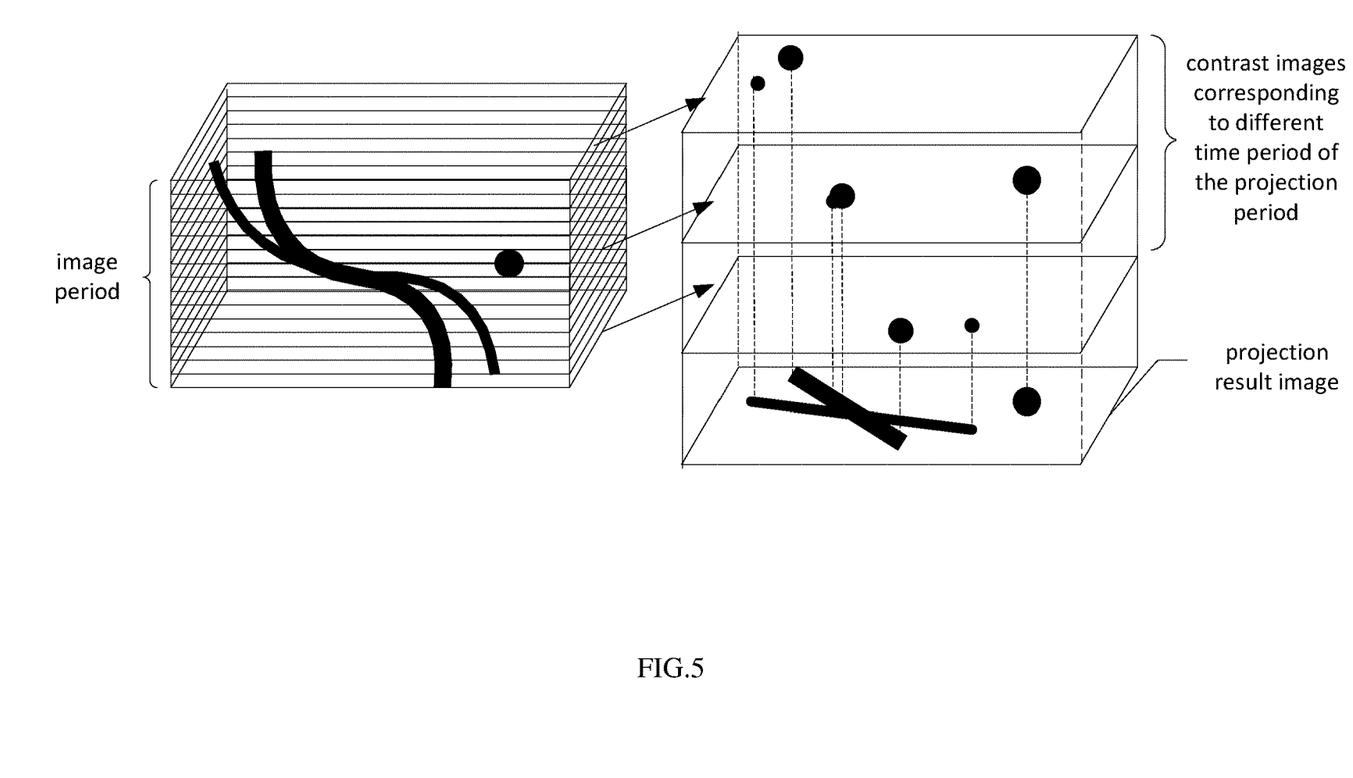
FIG. 5 is a diagram showing an imaging effect of the ultrasonic contrast imaging method according to embodiments of the present disclosure.

Please refer to FIG. 5, it is a diagram showing an imaging effect of the ultrasonic contrast imaging method according to embodiments of the present disclosure to using the image processing method according to an embodiment of the frame of imaging results projected image, which is flowing through the small blood vessels in contrast micro bubbles within the projection period k using maximum intensity projection (i.e., equation (4) shows the results)) after treatment, within a multi-frame image projection period, wherein the black bars and curve form a solid black dot in this multi-frame contrast image micro bubbles. In FIG. 5, in the upper right is the contrast within the image projected three different time period, the lowest level for the final results projected image projection period, we can see the contrast in the image at different times microbubble contrast dye shadow the resulting image projection connection, which is configured to detect small blood vessels.

In this embodiment, when the contrast microbubbles flow in the small blood vessels, the multi-frame contrast image micro bubbles are developing different dye film location, duration of treatment can make these images depict the flow trajectories contrast micro bubbles, which is small vascular morphology and other spatial information; continuous process by adjusting the time parameter (ie, the imaging process of projection period), the projected template changes over time, the results of ongoing projection image projected onto the template will be able to reflect the inflow and outflow of contrast micro bubbles time information, that is, the state of the small blood vessels filling subsided; by continuously adjusting the projection period also reflects the small blood vessels of different spatial and temporal information of scanned surfaces. In addition, the projection period is a fixed value, the accumulated error caused by the projection process only about the projection period, with the increase in the developing period is not increased; projection templates for any period within the projection of an image when the projection period changes, projection template naturally change and not static, so that the image projected continued on the template to better reflect the spatial information in the projection period to be currently detected objects as small vascular filling state subside.

Example 2:

Ultrasonic imaging process, the scanned image will inevitably produce movement of ultrasonic contrast imaging. Image motion may be due to human tissue with exercise-induced breathing or heartbeat, or it may be caused by movement of the ultrasound probe. Accordingly, there is the need for motion matching scanned images to reduce effects of image motion in ultrasonic imaging.

Figure 6:
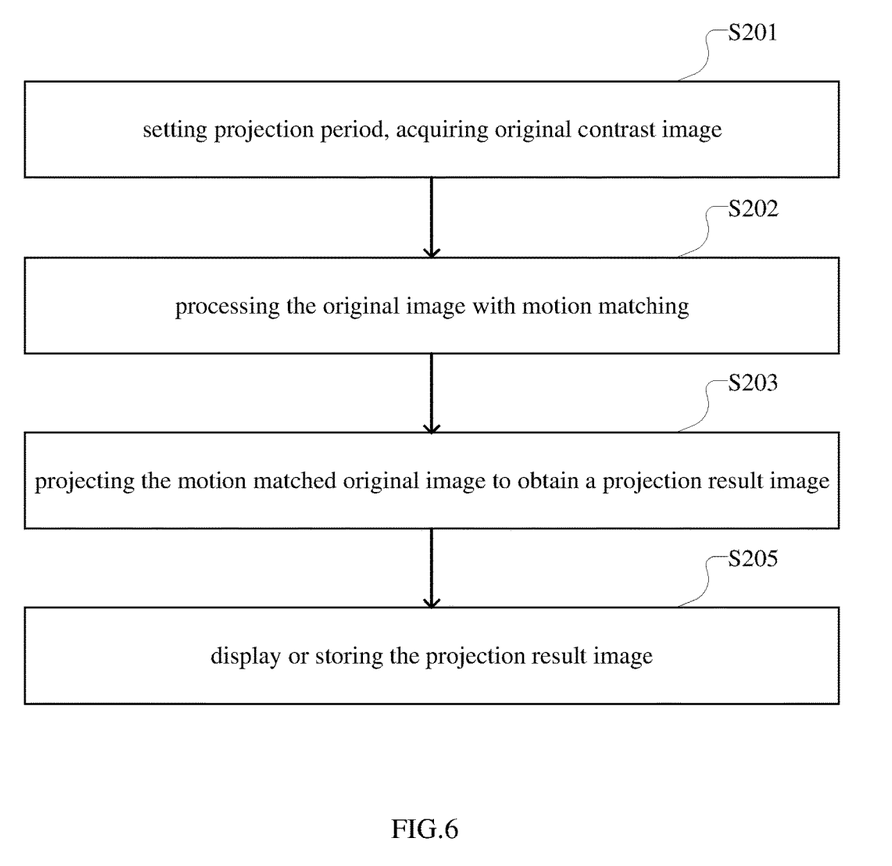
FIG. 6 is a schematic flow diagram of an ultrasonic contrast imaging method according to another embodiment of the present disclosure.

The ultrasonic contrast imaging method of the present embodiment includes the process steps of S201-S205:

The initial step S201, the step is similar to step S101 of Example 1, this not be repeated here. Motion registration step S202, N frames of the original contrast image obtained in step S201 registration exercise.

In particular ultrasonic imaging system/apparatus registration start movement or closing of this step may be implemented by various means, such as the system previously set in the original image data obtained after image registration start the motion correction process, Another example is the user can such as a keyboard, mouse, touch screen controls whether the motion registration via the input device, or ultrasonic device is started motion adaptive registration organ according to the scan or scan mode.

This step is the registration of the movement using video image processing algorithms can be commonly used in sports such as block matching registration method (Block Matching) method. To select the organization chart (B-mode image) motion image registration, for example, first select the motion tracking of the effective image area (ie, area of interest), calculated between two images trace block (Tracking Block) movement of displacement, then according to motion displacement tracking blocks interpolated frames between the two corresponding pixel displacement, and finally image correction based on the values of pixels of displacement. Here calculated displacement movement can also using conventional motion displacement calculation methods, such as simple tracking or cumulative tracking.

Figure 7:
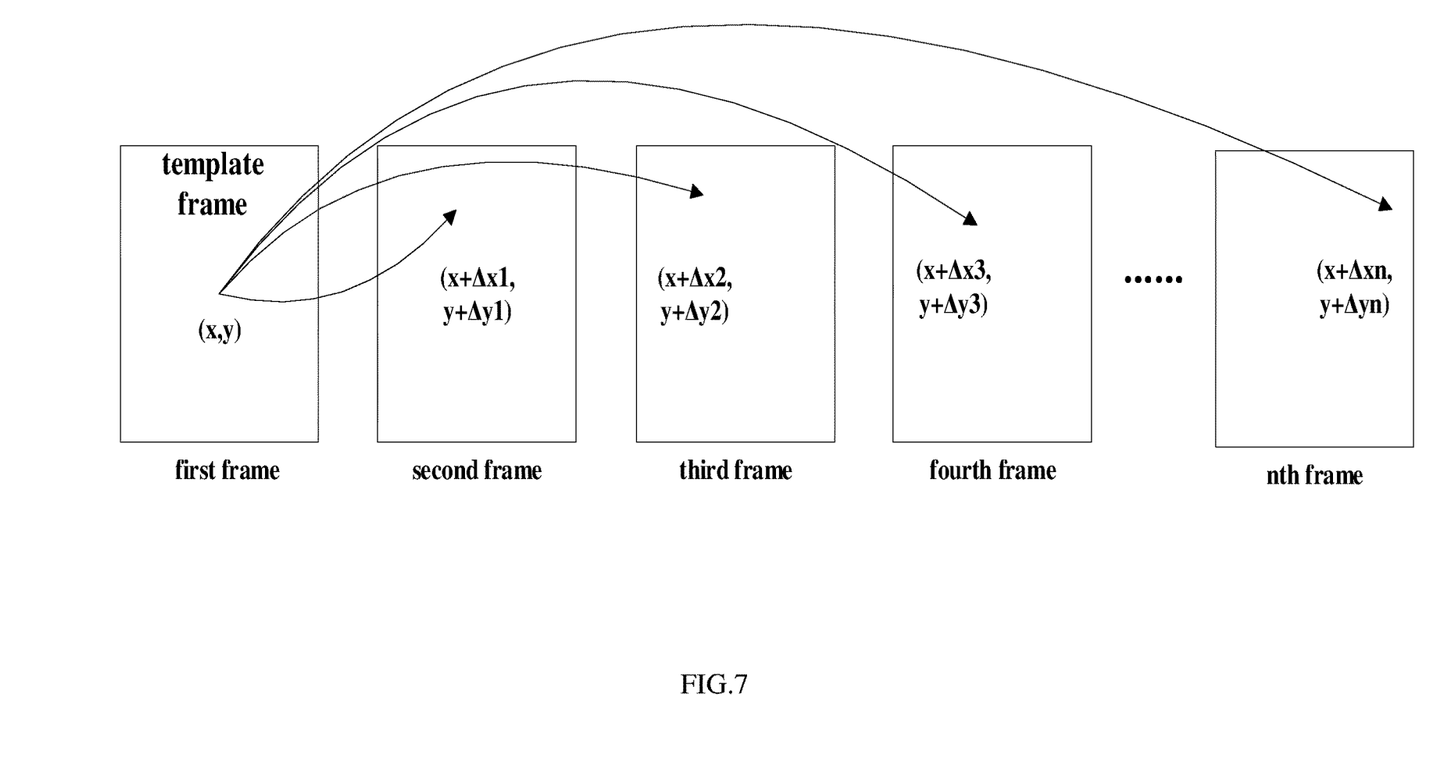
FIG. 7 is a principle diagram of calculating motion shift by a simple tracking method.

For the simple track, shown in FIG. 7, in a projection period (of n frames) in the projection to the first one template (i.e. template frame), the coordinates of a pixel in the template frame to (x, y), because of the movement, the pixels in the first two coordinates relative to the first one into $(x+\Delta x1, y+\Delta y1)$, in the first three in the coordinate position relative to the first one into $(x+\Delta x2, y+\Delta y2)$, followed by the n-th frame coordinate position relative to the first one becomes $(x+\Delta xn, y+\Delta yn)$, which is based on the coordinate position template frame pixel and the pixel coordinate position of each frame image obtained two frames displacement relative motion images, such as the first two displacement relative motion between frames and templates for the $(\Delta x1, \Delta y1)$. This simple method of tracking a simple calculation without accumulative error, i.e., the relative movement displacement current calculated that only the template frame image frame, but not to the other frame image, the disadvantage is the large range of motion and rapid tissue image, need to increase the search range, otherwise motion tracking failure, and for the organization of small amplitude and slow motion picture, the larger the search will lead to low efficiency.

Figure 8:
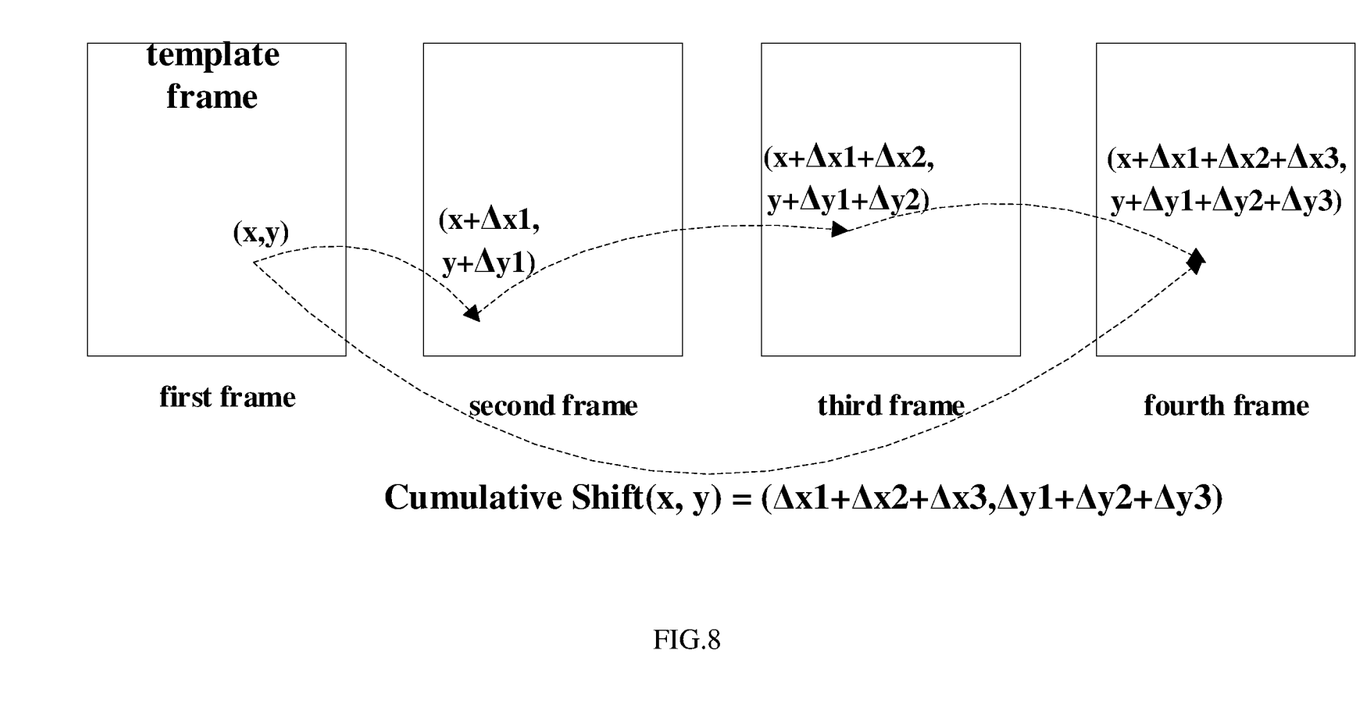
FIG. 8 is a principle diagram of calculating motion shift by a cumulative tracking method.

Cumulative track, 8, in a projection period (here assuming four image), is projected to a first template (i.e. template frame), the coordinates of a pixel in the template frame was (x, y), due to the presence of motion, the pixels in the first two of the coordinates relative to the first one into $(x+\Delta x1, y+\Delta y1)$, in the first three in the coordinate position relative to the first one is $(x+\Delta x1+\Delta x2, y+\Delta y1+\Delta y2)$, the pixels in the first four coordinate positions relative to the first one is $(x+\Delta x1+\Delta x2+\Delta x3, y+\Delta y1+\Delta y2+\Delta y3)$, that is, the coordinate position of the pixel in the current frame and the adjacent frame image coordinate position, can be displaced relative movement of adjacent frames, with the previous frame to obtain the relative displacement of the accumulated relative motion displacement prior frame image and the template frames. Cumulative advantage tracking method is applicable to a variety of organizations movement, small search range track blocks, so a small amount of calculation, high efficiency, but its drawback is the presence of accumulated error, and the increase will be more apparent with the projection periods.

Select the motion displacement calculation methods can be preset, or a user through input devices such as a keyboard, mouse, touch screen input control, adaptive ultrasound equipment can also be adjusted according to the scanning organ or scan mode. Example embodiments may be a region of interest in the whole image or partial image area, the image area selection method may be a partial block area of a predetermined system, either through user input devices such as a keyboard, mouse, touch screen input control, or ultrasound apparatus according to the organ or scan mode scanning adaptive adjustment.

With the reference time used by the motion image (i.e., image templates) may be the same projection imaging in step S203 will hereinafter be referred to with the projection of the template, or may be different, the selection may be pre-set the system, or by the user input devices such as a keyboard, mouse, touch screen input control, or ultrasound scanning device according to the organ or adaptive scanning mode. Registration reference motion picture can be tissue image data (ie, B-mode image), may also be a contrast image, it can also be a result of both the silhouette. The specific choice of visual reality may be, for example, select an organizational chart (B picture) to do motion tracking of the advantages of the reference image is the starting frame imaging process when no special requirements, the disadvantage is lower organizational chart contrast, the sensitivity and specificity insufficient; and choose to do motion tracking contrast image advantages reference contrast image contrast image is high, the disadvantage is the contrast microbubbles in the image flow impact tracing calculations, and it has called for the start frame to open when the imaging processing functions, Because there is no contrast image at an early stage when the contrast agent flows into the limited information not suitable template frame.

Projection imaging step S203, step S202 motion picture after registration projection imaging for specific process similar to Example 1 step S103 is similar, except that this time is for image motion after registration.

Thus, projection operation can be expressed as follows: outputPixel (x, y, n, k)=(inputPixel (x', y', n), inputPixel (x', y', n−1), . . . , inputPixel (x ', y', n−The difference k+1)) (5) (5) and (2) that, when the probe is relatively static organization, (X, y)=(x, y,), when the two since the image motion When the displacement, (x, y)=(x'+Δx, y'+Δy), i.e. the position of the movement after registration. Similarly, where the function f may be similar to that described in Example 1 the function f, except that this time inputPixel ( ) is the pixel with (x', y') of the associated pixel.

Examples of the projection period stalls in Example 1 is still selected, when the position "Auto", denotes the projection period adaptive value, corresponding to the projected image is not only the result of continuous projection result of adaptive systems, and also proposed a high-contrast microbubbles MI crushed or probe runaway introduction of interference and other image frames.

Displaying storage step S205, the projection image display or the results obtained in step S203 is stored, and the specific procedure of Example 1 is similar to step S105, not to repeat here.

Figure 9:
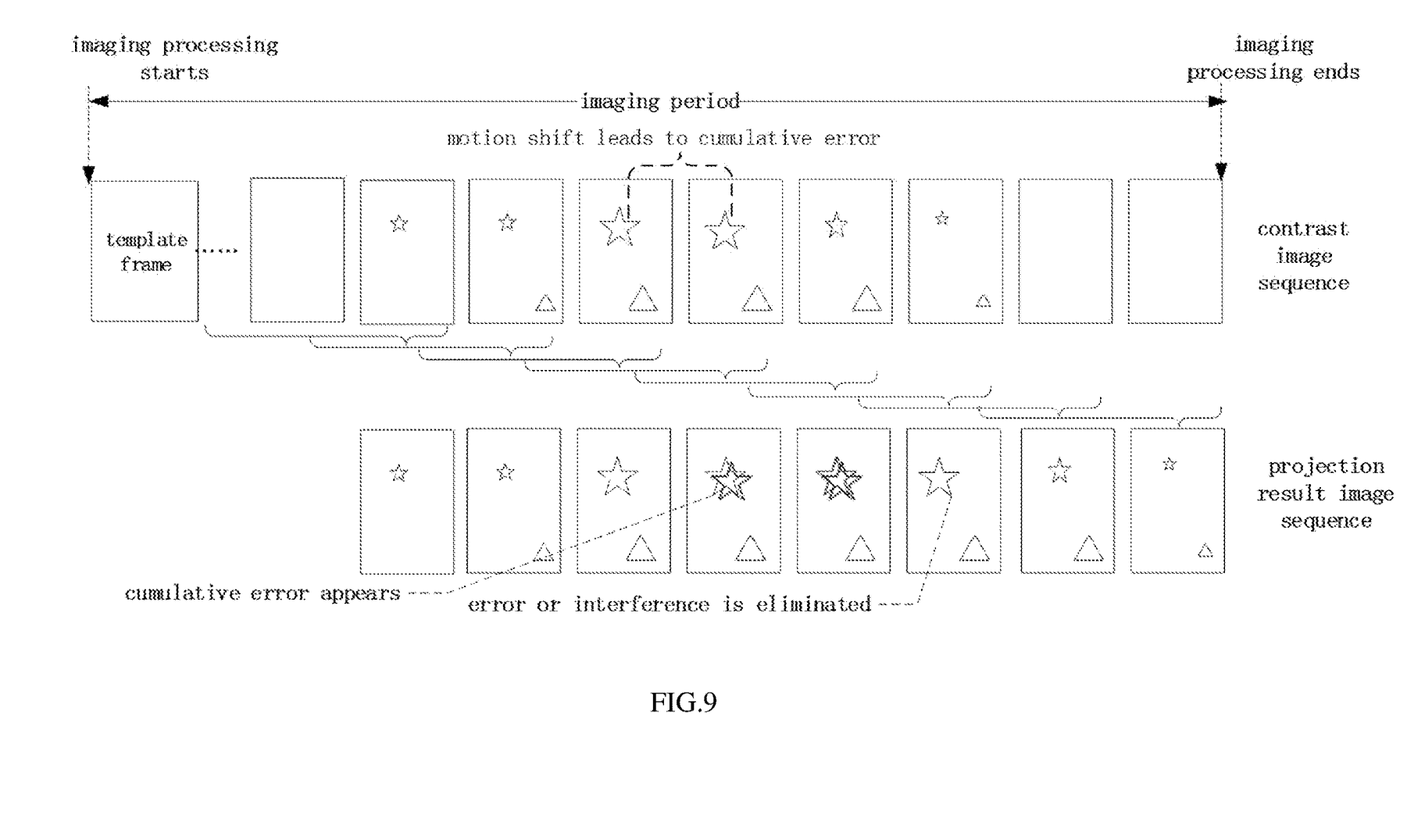
FIG. 9 is a diagram showing cumulative error in the displayed image is reduced or removed by using the ultrasonic contrast imaging method according to embodiments of the present disclosure.
Figure 10:
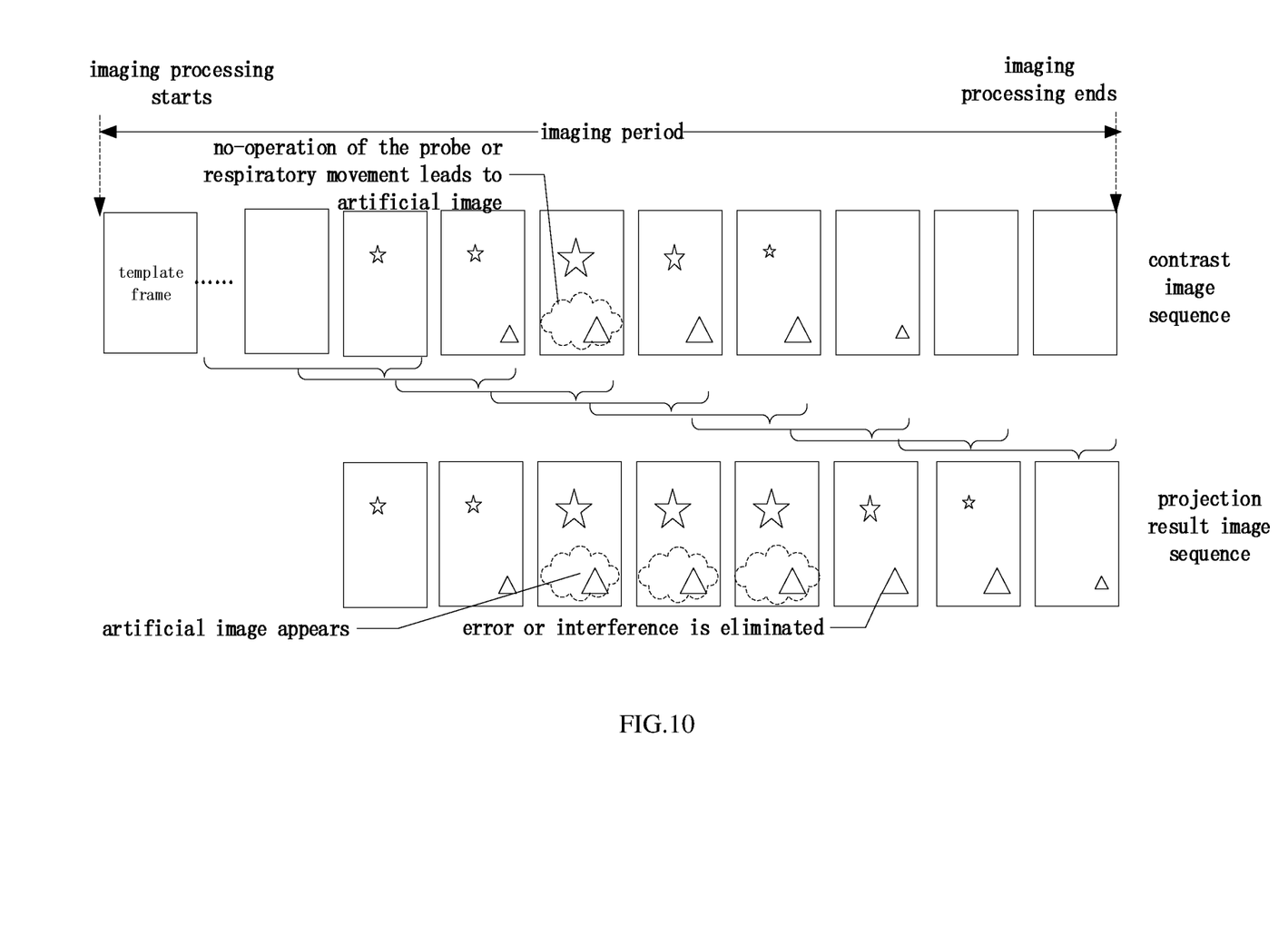
FIG. 10 is a diagram showing the artificial image in the displayed image is reduced or removed by using the ultrasonic contrast imaging method according to embodiments of the present disclosure.

FIG. 9 and FIG. 10 shows the results of Bian ultrasonic contrast imaging method of this embodiment is the continuous display can reduce or even eliminate the accumulated error or motion artifacts. Due to the need for a period of multi-frame ultrasonic imaging contrast images overlap, this time the move if the probe is moved or organization (such as breathing, heartbeat, the organization's own motion) and other situations which may result in blurred images (FIG. 9) or generating artifacts (see FIG. 10). If using conventional MIP image, the result will keep all accumulated error or artifact imaging period, this time, if a region of interest (ROI) is disturbed or cover up, you need to re-measure, patients spend more time and costs; and using the imaging method of this embodiment, the result can only be in a relatively short period of time (ie projection period, within the time shown in the inverted parentheses) are cumulative errors or artifacts interfere with or mask, and It will not affect the projected results of the other projection period, thus ensuring the image quality and because they save time and effort.

The advantage of this embodiment relate Example 1, the movement of the probe to further reduce or even eliminate the error, and improve the imaging quality of the imaging efficiency.

This disclosure example, using ultrasonic contrast imaging method fixed projection period, more than any projection template frame processing, technical characteristics are fixed projection period, and the projected template may change over time, the projection period specific values can be controlled by the user, or the system Default, or adaptively adjusted according to the scan mode and inspection organs. In addition, the continued accumulation of errors during imaging and motion tracking error and to effectively control and improve image quality.

Figure 11:
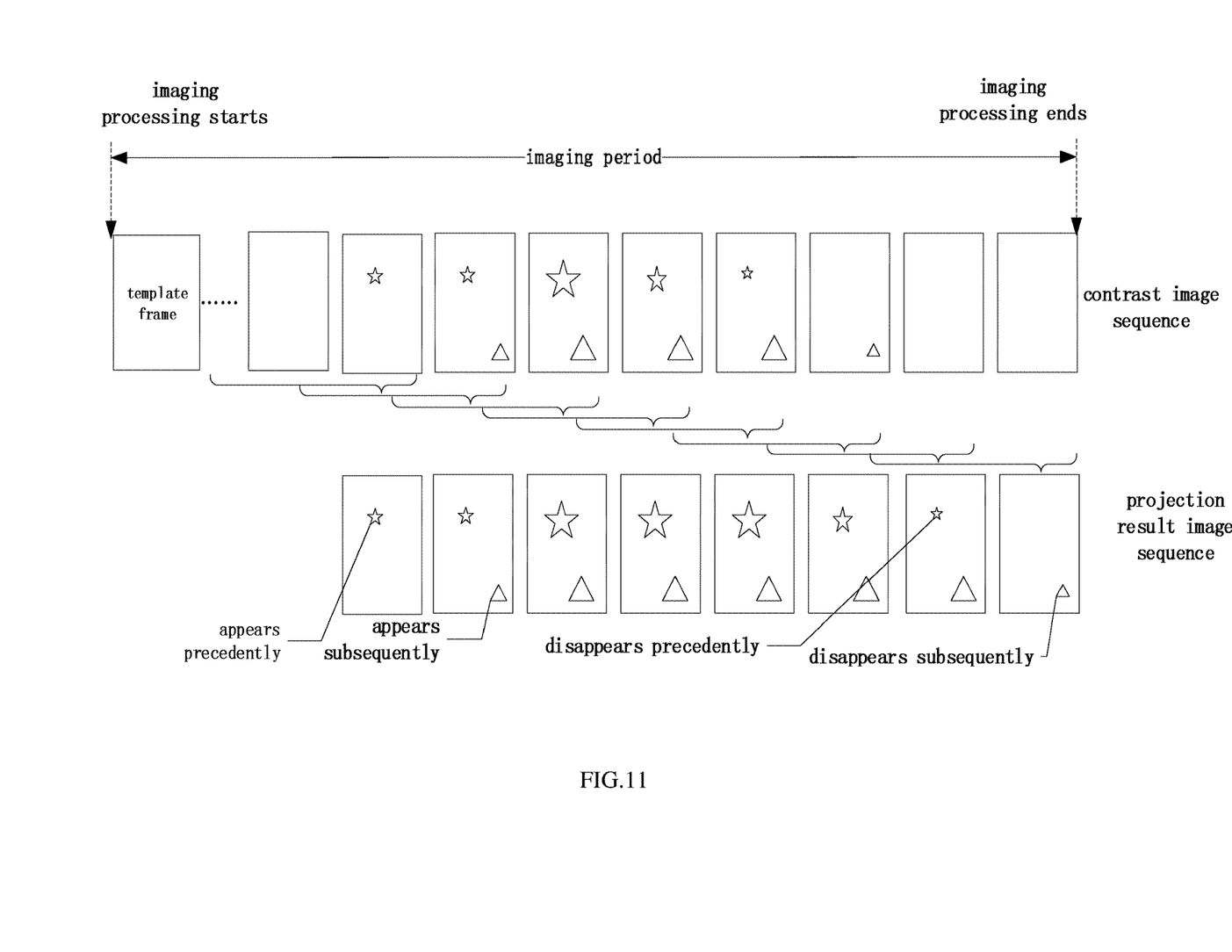
FIG. 11 is a diagram of continuously reflecting spatial and time phase information of small blood vessels.

MIP compared to conventional imaging methods, and projected results of imaging disclosures filed embodiment of the present ultrasonic contrast imaging apparatus or methods of either providing ultrasound images of the small blood vessels morphology of such spatial information, and can reflect the characteristics of vascular regression surplus time information (such as fast forward, rewind, slow forward full retreat, etc.); at the same time, the image of the projection period related to cumulative errors, will not increase imaging period increases, in addition, can also reduce or eliminate the cause of the probe moving image fuzzy, increase the contrast of blood vessels and tissues, improve imaging quality. 11, FIG. 11 shows using ultrasonic contrast imaging method of the present disclosure can be continuously reflect microvascular space and phase information of the results, which, when the five-pointed star logo Kuaijinkuaichu phase characteristics of the region and the triangle logo Jog slow time-out phase characteristics. Advantages of ultrasonic contrast imaging method of the present disclosure is a reflection of the scanning surface spatial information (position suspicious lesions and microvascular morphology), while providing more time information (such as a contrast agent relative to subside time) than conventional MIP imaging.

Those skilled in the art can appreciate that the above-described embodiment, all or part of the steps of various methods can be by a program instructing related hardware, the program may be stored in a computer-readable storage medium, the storage medium may include: a read-only memory, RAM, disk, or CD-ROM.

More than the disclosure of a specific example of the present invention will be described, but to aid in understanding the present invention is not intended to limit the present invention. Those of ordinary skill in the art, according to the idea of the present invention, the above specific embodiments change.

What is claimed is:

1. An ultrasonic contrast imaging method comprising:
    an initial step for acquiring N frames of contrast image, wherein N is the total number of frames gathered within an imaging period;
    projection imaging step for projecting the N frames of contrast image to obtain projection result image of the N frames of contrast image, wherein an nth group of original contrast image less than the N frames of contrast image is projected in a projection template to obtain a projection result image of an nth frame of original contrast image, wherein the projection template is one frame of the nth group of original contrast image, and n is a positive integer greater than or equal to 1 and less than N, wherein the nth group of original contrast images is projected within a projection period of an adjustable projection period for projecting the N frames of contrast image and comprises a plurality of frames of original contrast images including the nth original contrast image, and wherein the projection period is a value less than the imaging period of gathering the N total number of frames that is set from the adjustable projection period for projecting the N frames of contrast image once the value is designated from the adjustable projection period; and
    a display and/or storage step for displaying or storing the projection result image of the N frames of original contrast image.

2. The ultrasonic contrast imaging method according to claim 1, wherein projection periods of different groups of original contrast image are identical or different in the projection imaging step, and the projection period is a predetermined length of time period or a predetermined number of continuous frames of the original contrast image.

3. The ultrasonic contrast imaging method according to claim 2, wherein the projection imaging step using the equation of:

$$\text{outputPixel}(x,y,n,k)=f(\text{inputPixel}(x,y,n), \text{inputPixel}(x,y,n-1), \ldots, \text{inputPixel}(x,y,n-k+1))$$

Wherein, outputPixel(x, y, n, k) represents the gray value of the pixel with coordinate (x, y) in the nth frame of the projection result image, k represents the total number of frames of the projection period, f( ) denotes a function relationship, inputPixel (x, y, n) represents a gray value of the pixel with coordinate (x, y) in the nth frame of the original contrast image, inputPixel (x, y, n−1) represents a gray value of the pixel with coordinate (x, y) in the (n−1)th frame of the original contrast image, and inputPixel (x, y, n−k+1) represents a gray value of the pixel with coordinate (x, y) in the (n−k+1)th frame of the original contrast image.

4. The ultrasonic contrast imaging method according to claim 1, wherein the method further comprising a motion registration step for motion registering each frame of the N frames of original contrast image.

5. The ultrasonic contrast imaging method according to claim 4, wherein the projection imaging step uses the equation of:

$$\text{outputPixel}(x,y,n,k)=f(\text{inputPixel}(x',y',n), \text{inputPixel}(x',y',n-1), \ldots, \text{inputPixel}(x',y',n-k+1))$$

Wherein, outputPixel(x, y, n, k) represents the gray value of the pixel with coordinate (x, y) in the nth frame of the projection result image, k represents the total number of frames of the projection period, f( ) denotes a function relationship, inputPixel(x',y',n) represents a gray value of the pixel with coordinate (x',y') in the nth frame of the original contrast image, inputPixel (x',y', n−1) represents a gray value of the pixel with coordinate (x',y') in the (n−1)th frame of the original contrast image, and inputPixel (x',y', n−k+1) represents a gray value of the pixel with coordinate (x',y') in the (n−k+1th) frame of the original contrast image, the pixel with coordinate (x,y) of the nth frame of the projection result image corresponds to the pixel with coordinate (x',y') of the nth frame of the original contrast image being motion registered.

6. The ultrasonic contrast imaging method according to claim 2, wherein the function relationship is chosen from time domain weighted integral operations related to image information.

7. An ultrasonic contrast imaging apparatus comprising:
    an original image acquisition unit for emitting ultrasonic pulse to a target object, receiving ultrasonic echo signals returned by the target object, and performing signal processing to the received ultrasonic echo signals to obtain N frames of contrast image, wherein N is the total number of frames gathered within an imaging period;

a projection imaging unit for projecting the N frames of contrast image to obtain projection result image of the N frames of contrast image, wherein an nth group of original contrast image less than the N frames of contrast image is projected in a projection template to obtain a projection result image of an nth frame of original contrast image, wherein the projection template is one frame of the nth group of original contrast image, and n is a positive integer greater than or equal to 1 and less than N, wherein the nth group of original contrast images is projected within a projection period of an adjustable projection period for projecting the N frames of contrast image and comprises a plurality of frames of original contrast images including the nth original contrast image, and wherein the projection period is a value less than the imaging period of gathering the N total number of frames that is set from the adjustable projection period for projecting the N frames of contrast image once the value is designated from the adjustable projection period; and a display/storage unit for displaying or storing the projection result image of the N frames of original contrast image.

8. The ultrasonic contrast imaging apparatus according to claim 7, wherein projection periods of different groups of original contrast image are identical or different in the projection imaging unit, and the projection period is a predetermined length of time period or a predetermined number of continuous frames of the original contrast image.

9. The ultrasonic contrast imaging apparatus according to claim 7, further comprises a motion registration unit for motion registering each frame of the N frames of original contrast image.

10. The ultrasonic contrast imaging apparatus according to claim 9, wherein the projection imaging unit uses the equation of:

$$\text{outputPixel}(x,y,n,k) = f(\text{inputPixel}(x',y',n), \text{inputPixel}(x',y',n-1), \ldots, \text{inputPixel}(x',y',n-k+1))$$

Wherein, outputPixel(x, y, n, k) represents the gray value of the pixel with coordinate (x, y) in the nth frame of the projection result image, k represents the total number of frames of the projection period, f( ) denotes a function relationship, inputPixel(x',y',n) represents a gray value of the pixel with coordinate (x',y') in the nth frame of the original contrast image, inputPixel (x',y', n−1) represents a gray value of the pixel with coordinate (x',y') in the (n−1)th frame of the original contrast image, and inputPixel (x',y', n−k+1) represents a gray value of the pixel with coordinate (x',y') in the (n−k+1)th frame of the original contrast image, the pixel with coordinate (x,y) of the nth frame of the projection result image corresponds to the pixel with coordinate (x',y') of the nth frame of the original contrast image being motion registered.

11. The ultrasonic contrast imaging apparatus of claim 9, wherein the motion registration unit is configured to motion register each frame of the N frames of original contrast image through cumulative tracking.

12. The ultrasonic contrast imaging apparatus of claim 11, wherein the motion registration unit is configured to motion register each frame of the N frames of original contrast image by tracking displacements of a pixel across two or more adjacent frames of the N frames of original contrast image, wherein the displacement of the pixel across the two or more adjacent frames of the N frames of original contrast image are used to motion register at least a subset of each frame of the N frames of the original contrast image.

13. The ultrasonic contrast image apparatus of claim 12, wherein the displacement of the pixel across the two or more adjacent frames of the N frames of original contrast image are used to motion register at least a subset of each frame of the N frames of the original contrast image corresponding to the two or more adjacent frames.

14. The ultrasonic contrast imaging apparatus of claim 11, wherein the motion registration unit is configured to motion register each frame of the N frames of original contrast image through cumulative tracking during at least a portion of the projection period.

15. The ultrasonic contrast imaging apparatus according to claim 8, wherein the projection imaging unit uses the equation of:

$$\text{outputPixel}(x,y,n,k) = f(\text{inputPixel}(x',y',n), \text{inputPixel}(x',y',n-1), \ldots, \text{inputPixel}(x',y',n-k+1))$$

Wherein, outputPixel(x, y, n, k) represents the gray value of the pixel with coordinate (x, y) in the nth frame of the projection result image, k represents the total number of frames of the projection period, f( ) denotes a function relationship, inputPixel(x',y',n) represents a gray value of the pixel with coordinate (x',y') in the nth frame of the original contrast image, inputPixel (x',y', n−1) represents a gray value of the pixel with coordinate (x',y') in the (n−1)th frame of the original contrast image, and inputPixel (x',y', n−k+1) represents a gray value of the pixel with coordinate (x',y') in the (n−k+1th) frame of the original contrast image, the pixel with coordinate (x,y) of the nth frame of the projection result image corresponds to the pixel with coordinate (x',y') of the nth frame of the original contrast image being motion registered.

* * * * *